(12) United States Patent
Gonzalez (10) Patent No.: US 10,085,430 B1
(45) Date of Patent: Oct. 2, 2018

(54) AQUARIUM FILTRATION AND ALGAE CONTROL SYSTEM

(71) Applicant: Ernest Gonzalez, Bronx, NY (US)

(72) Inventor: Ernest Gonzalez, Bronx, NY (US)

(*) Notice: Subject to any disclaimer, the term of this patent is extended or adjusted under 35 U.S.C. 154(b) by 0 days.

(21) Appl. No.: 15/460,830

(22) Filed: Mar. 16, 2017

(51) Int. Cl.
| | |
|---|---|
| *A01K 63/04* | (2006.01) |
| *B01D 29/56* | (2006.01) |
| *C02F 3/32* | (2006.01) |
| *C12M 1/00* | (2006.01) |
| *C12M 1/12* | (2006.01) |
| *A01K 63/10* | (2017.01) |
| *A01G 33/00* | (2006.01) |
| *C02F 101/16* | (2006.01) |
| *C02F 103/20* | (2006.01) |

(52) U.S. Cl.
CPC ............ *A01K 63/045* (2013.01); *A01G 33/00* (2013.01); *A01K 63/10* (2017.01); *B01D 29/56* (2013.01); *C02F 3/322* (2013.01); *C12M 21/02* (2013.01); *C12M 25/06* (2013.01); *C02F 2101/163* (2013.01); *C02F 2103/20* (2013.01); *C02F 2203/006* (2013.01); *C02F 2303/20* (2013.01)

(58) Field of Classification Search
CPC ..... A01K 63/045; A01K 63/10; C12M 21/02; C12M 25/06; A01G 33/00; B01D 29/56; C02F 3/322; C02F 2303/20; C02F 2101/163; C02F 2103/20; C02F 2203/006
USPC ..... 210/602, 631, 167.222, 167.27; 119/259, 119/260
See application file for complete search history.

(56) References Cited

U.S. PATENT DOCUMENTS

| | | | | |
|---|---|---|---|---|
| 3,723,304 | A | * | 3/1973 | Storck ................. A01K 63/045 210/151 |
| 3,943,659 | A | | 3/1976 | Katz |
| 5,097,795 | A | * | 3/1992 | Adey .................... A01K 63/04 119/226 |
| 5,176,100 | A | * | 1/1993 | Fujino ................... A01K 63/04 119/227 |
| 5,536,398 | A | | 7/1996 | Reinke |
| 5,799,612 | A | | 9/1998 | Page |
| 5,965,016 | A | | 10/1999 | Suchowski et al. |
| 7,442,306 | B2 | | 10/2008 | Olivier |
| 2003/0213745 | A1 | * | 11/2003 | Haerther .................. C02F 3/32 210/602 |
| 2005/0133423 | A1 | * | 6/2005 | Olivier .................. A01K 63/04 210/167.22 |

(Continued)

FOREIGN PATENT DOCUMENTS

| | | |
|---|---|---|
| WO | WO2005033019 | 4/2005 |
| WO | WO2011089077 | 7/2011 |
| WO | WO2013101775 | 7/2013 |

*Primary Examiner* — Fred Prince
(74) *Attorney, Agent, or Firm* — Goldstein Law Offices, P.C.

(57) ABSTRACT

An aquarium filtration and algae control system, for use with an aquarium containing a quantity of water, having a housing having a growth chamber and an overflow part. The growth chamber includes at least two cells separated by at least one photocontactor wall. Water from the aquarium is sprayed into each of the cells to create circuitous high velocity water flow and each cell and each photocontactor wall is illuminated by a high intensity light source to promote diatom algae growth within the growth chamber and thereby prevent undesirable algae growth elsewhere in the aquarium.

20 Claims, 8 Drawing Sheets

(56) References Cited

U.S. PATENT DOCUMENTS

2015/0027938 A1    1/2015   Farrish
2017/0127656 A1*   5/2017   Bee ..................... A01K 63/006

* cited by examiner

AQUARIUM FILTRATION AND ALGAE CONTROL SYSTEM

TECHNICAL FIELD

The present disclosure relates generally to an aquarium filtration system. More particularly, the present disclosure relates to a system that simultaneously promotes water composition that is healthy for fish while preventing undesirable algae growth on aquarium surfaces.

BACKGROUND

Maintaining an aquarium can be both rewarding and time consuming. Successful aquarium maintenance requires both providing an authentic and aesthetic microcosm for the enjoyment of the hobbyist and providing suitable conditions that allows fish, invertebrates, and other aquarium life to thrive. Among these conditions are temperature, salinity (for marine aquariums), and balance of nutrients and toxins. When certain nutrient levels get too high, they can become toxic or promote other undesirable biological processes.

Biological filtration systems have been used for decades as a way to regulate the concentration of nutrients. As an example, fish produce ammonia as waste. Nitrosomona bacteria develop in common biological filtration systems to convert the ammonia into nitrites. While nitrites are not as harmful to fish and invertebrates as ammonia, at higher concentrations they can be. Luckily, the increased levels of nitrites cause other bacteria such as *Nitrobacter* to thrive within the biological filtration system, as such bacteria ingest nitrites and convert them to nitrates.

Nitrates can be toxic to fish at higher concentrations. They are difficult to remove, and often require partial water changes. Also their presence at high levels has another undesirable effect: it promotes algae growth.

Once algae begins to grow in an aquarium, it will quickly cover every hard surface. Most noticeable and dismaying to the aquarium hobbyist is the growth of algae on the tank glass. Algae growth on glass is both unsightly and interferes with enjoyment of the aquarium.

Certain devices, processes, and filters have been devised that attempt to separately reduce nitrate levels, and control algae growth. While these units may be suitable for the particular purpose employed, or for general use, they would not be as suitable for the purposes of the present disclosure as disclosed hereafter.

In the present disclosure, where a document, act or item of knowledge is referred to or discussed, this reference or discussion is not an admission that the document, act or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed and it is contemplated that the claims may encompass one or more of the conventional technical aspects discussed herein.

BRIEF SUMMARY

An aspect of an example embodiment in the present disclosure is to provide an aquarium filtration system that prevents undesirable growth of algae on tank glass and other aquarium surfaces. Accordingly, the system described herein promotes diatom algae growth within the filtration system so that the diatoms are the dominant algae within the aquarium and as a result other algae does not grow on tank glass and other aquarium surfaces.

It is another aspect of an example embodiment in the present disclosure to provide a system that effectively promotes algae growth within the filtration system. Accordingly, the system includes a growth chamber having photocontactor walls made of translucent material. The nutrient balance within the water is maintained such that it is dominated by silica, followed by phosphate. Silicate dominance may be created by introducing a silicate such as sodium silicate for marine aquariums and potassium silicate for fresh water aquariums. A light source illuminates the growth chamber with intense light. Aquarium water is introduced into the growth chamber at a high velocity to create a swirling vortex of water therein. With ideal conditions thus created for the growth of benthic diatom algae, the photocontactor walls readily become covered in a biofilm of benthic diatom algae.

It is yet another aspect of an example embodiment in the present disclosure to provide an aquarium filtration system that maintains a water composition that is healthy for fish and other aquarium life, and will even withstand a high bio-load created when the aquarium is overstocked with fish. Accordingly, the diatom algae removes nitrates and other nutrients that could otherwise be harmful to marine life.

It is still another aspect of an example embodiment that the growth chamber is easy to clean. Accordingly, a drain assembly is provided at the bottom of the growth chamber that is generally closed with a drain valve. When cleaning the growth chamber, the valve is opened so that harvested algae may be flushed out through the valve rather than introducing it into the aquarium and without requiring the physical removal of the growth chamber.

Accordingly, the present disclosure describes an aquarium filtration and algae control system, for use with an aquarium containing a quantity of water, having a housing having a growth chamber and an overflow part. The growth chamber includes at least two cells separated by at least one photocontactor wall. Water from the aquarium is sprayed into each cell to create circuitous high velocity water flow and each cell and each photocontactor wall is illuminated by a high intensity light source to promote diatom algae growth within the growth chamber and thereby prevent undesirable algae growth elsewhere in the aquarium.

The present disclosure addresses at least one of the foregoing disadvantages. However, it is contemplated that the present disclosure may prove useful in addressing other problems and deficiencies in a number of technical areas. Therefore, the claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

BRIEF DESCRIPTION OF THE DRAWINGS

In the drawings, like elements are depicted by like reference numerals. The drawings are briefly described as follows.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete and fully conveys the scope of the present disclosure to those skilled in the art.

DETAILED DESCRIPTION OF THE PREFERRED EMBODIMENTS

Figures 1, 1A:
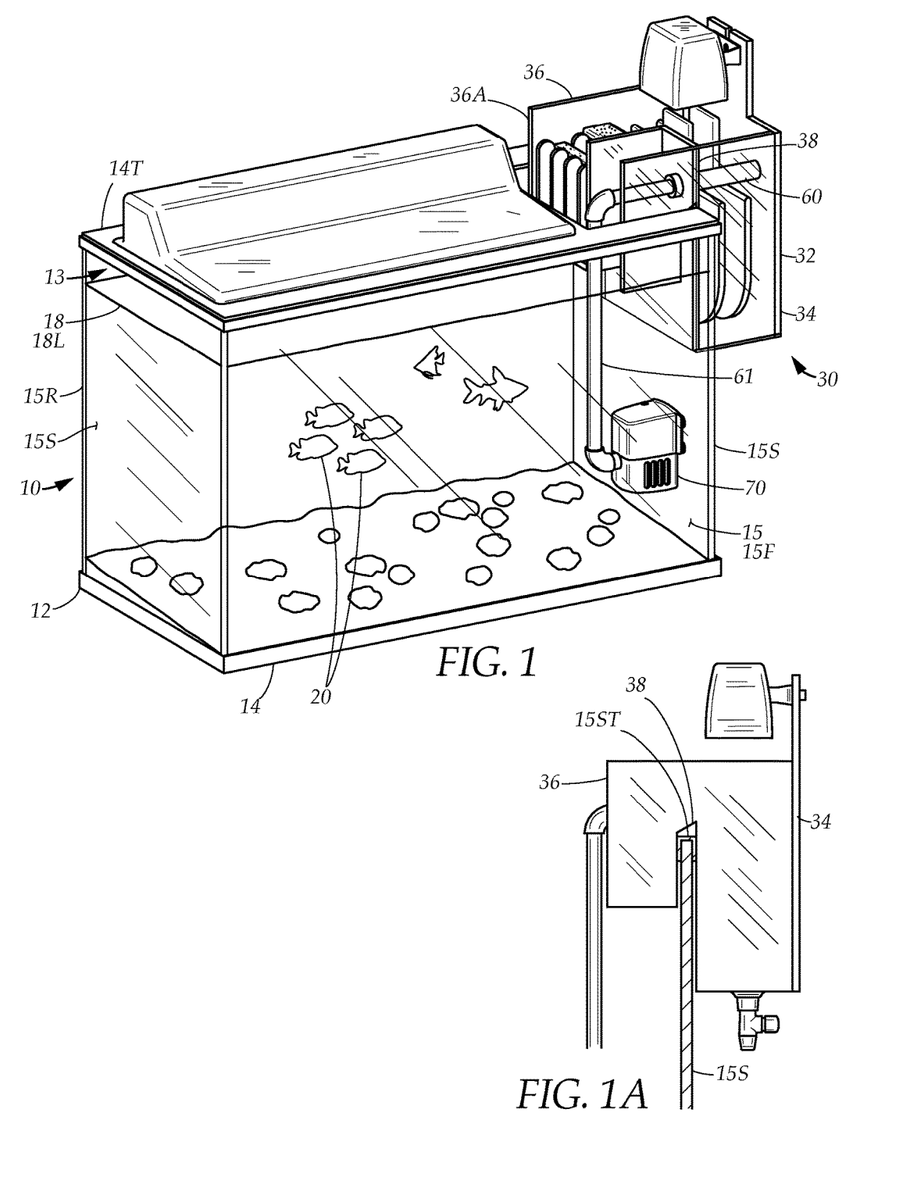
FIG. 1 is diagrammatic perspective view, showing an aquarium having the filtration system in accordance with the present disclosure.
FIG. 1A is a side elevational view with parts broken away, illustrating the filtration system resting on the aquarium tank.

FIG. 1 illustrates an aquarium 10. The aquarium includes a tank 12 having a frame 14 including a frame top 14T. The tank 12 also includes glass panels 15, including a front 15F, a rear 15R, and a pair of sides 15S. The tank 12 has a tank interior 13 capable of holding a quantity of water 18 for sustaining fish 20 and other marine life. The water 18 has a water level 18L that is near the frame top 14T. The aquarium 10 may be a fresh water or marine environment. Referring momentarily to FIG. 1A, one of the sides 15S is illustrated having a side top edge 15ST.

In accordance with principles of the present disclosure, a filtration system 30 is provided to work in conjunction with the aquarium 10 to help provide sustainable conditions for the fish 20 and other life within the aquarium 10. The filtration system 30 includes a housing 32 that is configured to attach onto the tank 12, near the frame top 14T along one of the sides 15S. In particular, referring to FIG. 1 and FIG. 1A, the housing 32 includes a growth chamber 34 that extends outside of the tank 12, an overflow part 36 that extends within the frame and into the interior 13, and a transition part 38 that extends between the overflow part 36 and growth chamber 34. The transition part 38 rests upon the side top edge 15ST of one of the sides and is supported thereby. Accordingly, the housing 32 of the filtration system 30 is supported by the tank 12 at the frame top 14T.

Figures 2, 2A:
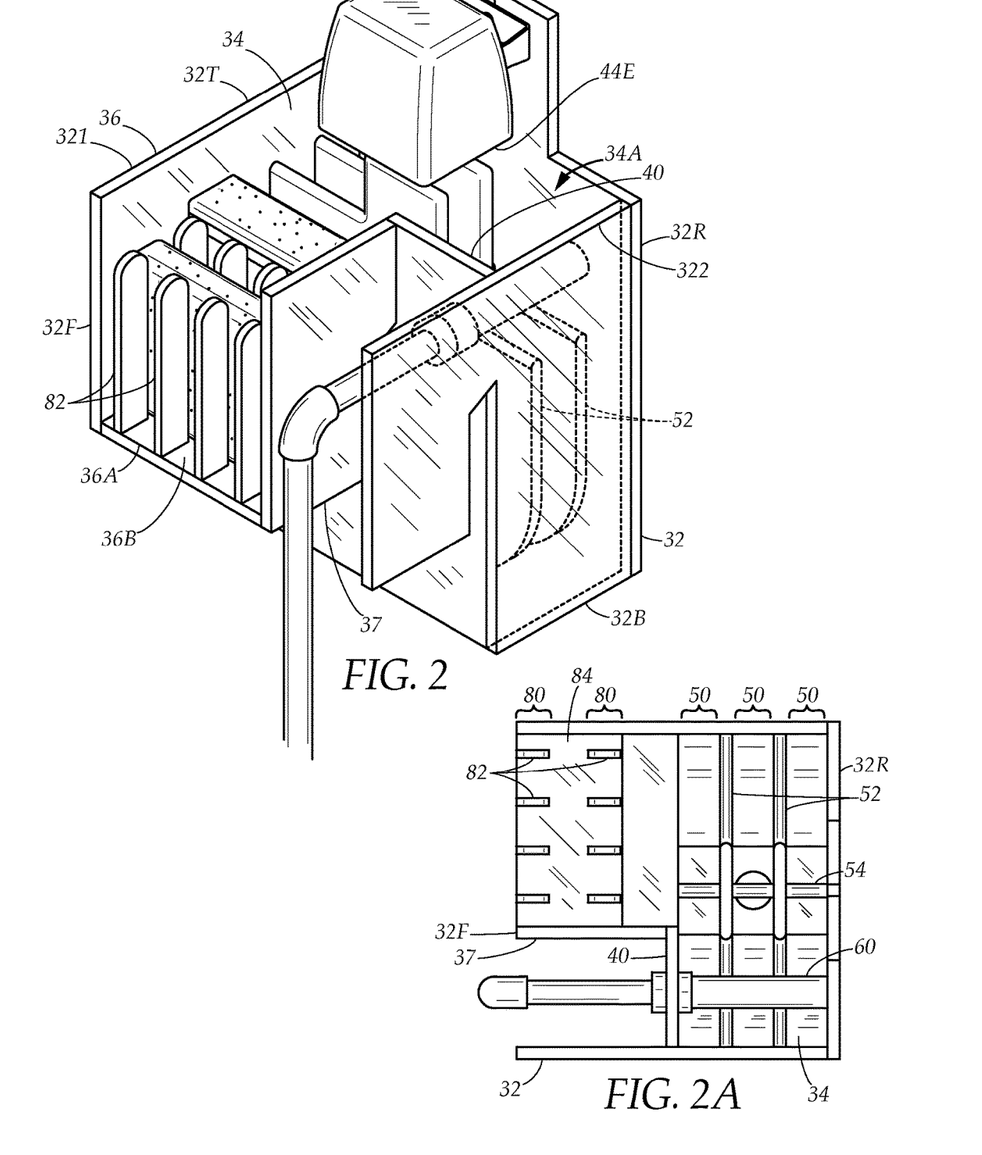
FIG. 2 is a diagrammatic perspective view, illustrating just the filtration system, per se.
FIG. 2A is a top plan view, illustrating the growth chamber and the overflow part of the filtration system.

FIG. 2 and FIG. 2A illustrate the housing 32, including a housing top 32T, a housing bottom 32B, a housing front 32F and a housing rear 32R, and first side 321 and a second side 322. The housing 32 is composed substantially of transparent materials such as plastic. The housing includes an intermediate wall 40 located midway between the housing rear 32R and housing front 32F. The intermediate wall 40 also extends between the growth chamber 34 and overflow part 36 and has a wall height as it extends between the growth chamber 34 and overflow part 36 that establishes a water level in the growth chamber 34 such that water flows over the intermediate wall 40 into the overflow part 36 and is reintroduced into the interior 13 of the aquarium 10. The chamber 34 defines a chamber interior 34A between the first side 321, second side 322, housing rear 32R and intermediate wall 40, capable of containing a volume of water. The overflow part 36 includes an overflow bottom 36B that may be higher than the housing bottom 32B. The overflow part 36 is defined between the housing front 32F and the intermediate wall 40, and between the housing first side 321 and an overflow inside wall 37. The housing rear 32R includes a lamp support 42 that extends upwardly from the housing top 32T. A light source 44 having an output end 44E is attached to the lamp support 42 such that the output end 44E is cantilevered over the growth chamber 34. The light source 44 directs high intensity light downwardly onto the growth chamber 34 to facilitate growth of diatoms therein as will be described in detail hereinbelow. The light source 44 may include a matrix of LEDs, such as a fifty watt LED matrix. The light source 44 may be selectively activated using a timer that is programmed to provide an illumination schedule that is optimized for facilitating growth of diatom algae.

The growth chamber 34 includes a plurality of cells 50 that are separated by photocontactor walls 52 that extend vertically within the growth chamber 34. The photocontactor walls 52 extend substantially parallel to the housing rear 32R and intermediate wall 40 and substantially between the first side 321 and second side 322. Note that the cell 50 closest to the housing rear 32R is defined between the housing rear 32R and the nearest of the photocontactor walls 52. The cell closest to the intermediate wall 40 is defined between the intermediate wall 40 and the nearest of the photocontactor walls 52. A diverter 54 extends transversely across each of the cells 50, between the housing rear 32R and intermediate wall 40, substantially centered between the first side 321 and second side 322. Note that the diverter 54 may be configured as individual diverters 54 that each extend across only one of the cells, or may be a single diverter that traverses all of the cells, in a spindle-like fashion.

Figure 5B:
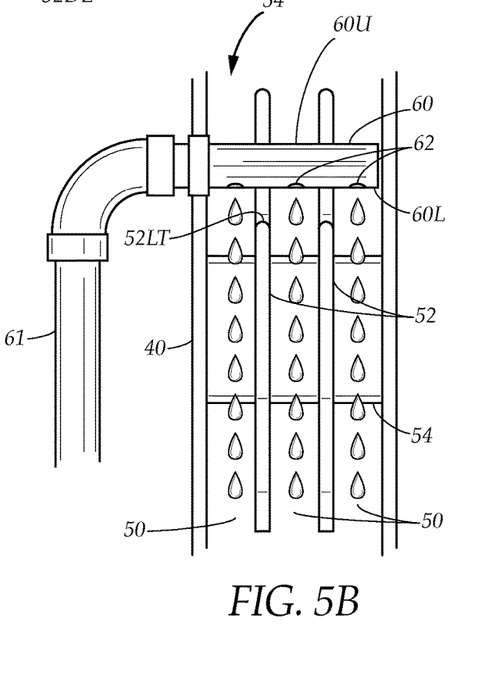
FIG. 5B is a side elevational view with parts broken away, illustrating the influent spray bar in conjunction with the growth chamber, illustrating three cells created by the photocontactor walls, each of the three cells aligned with one of the spray openings of the influent spray bar.
Figure 6:
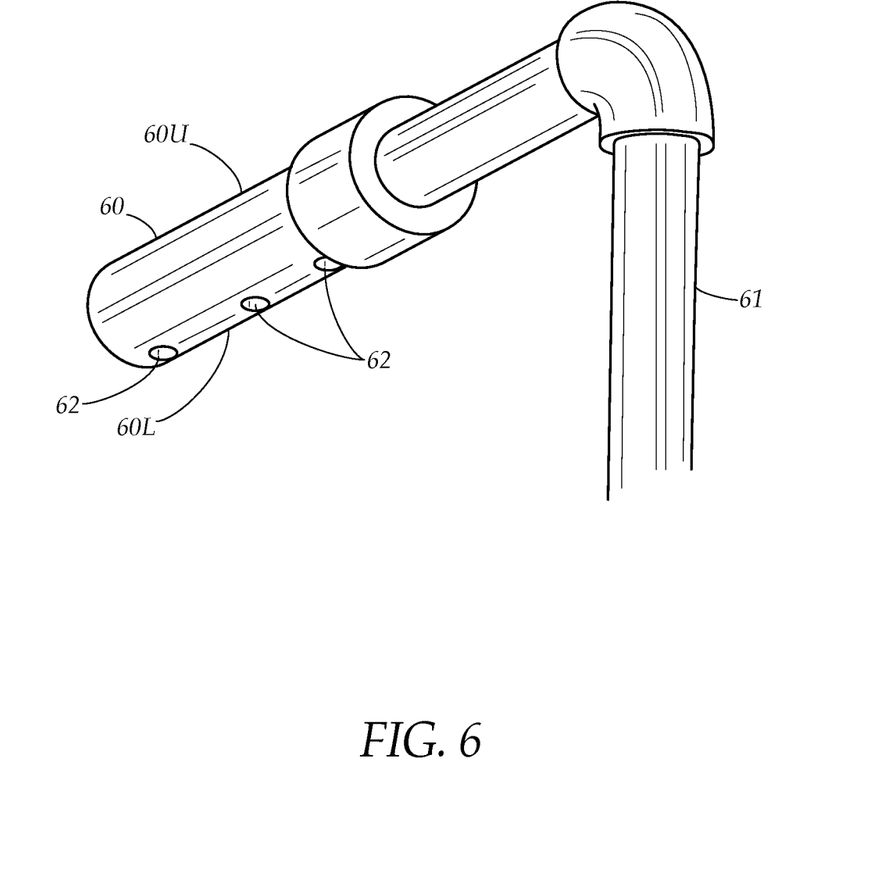
FIG. 6 is a diagrammatic perspective view, illustrating just the spray bar and influent tube.
Figures 7A, 7B:
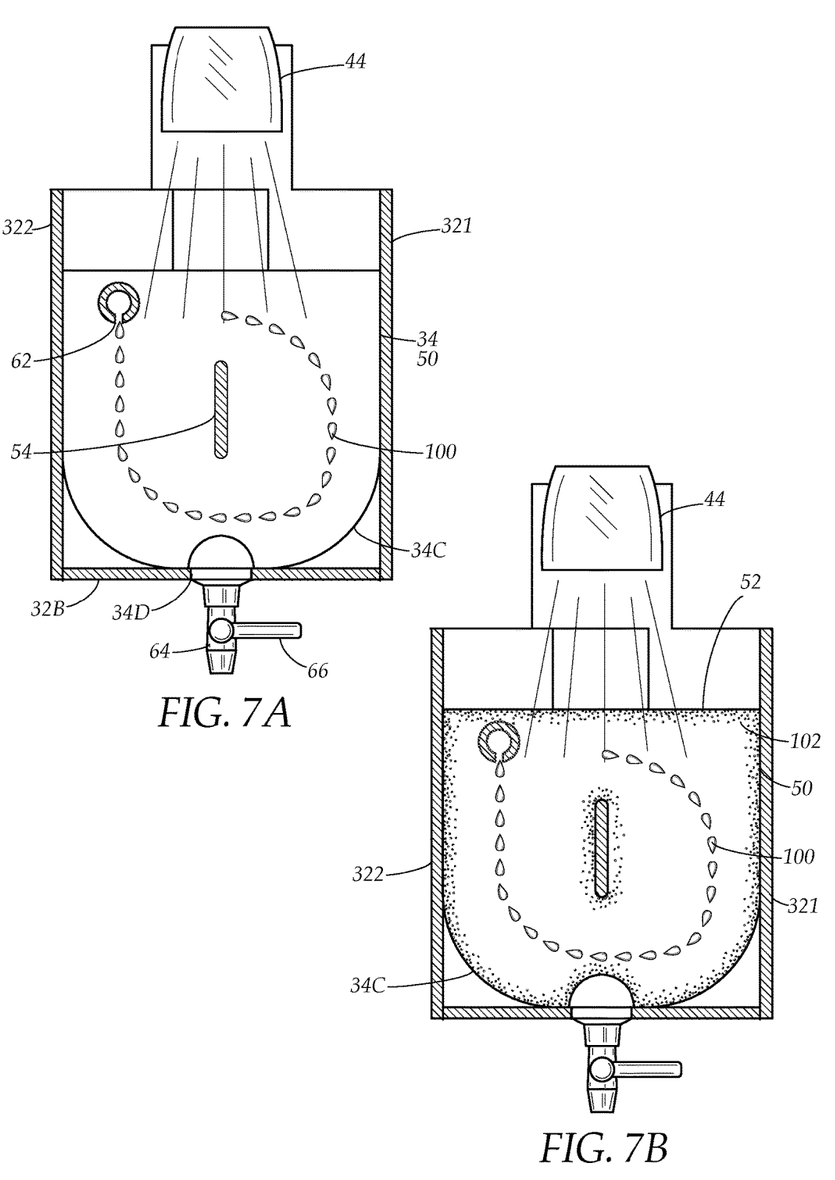
FIG. 7A is a front elevational view with parts broken away, illustrating one of the cells, under the influence of the illumination lamp, and illustrating a vortex of circuitous water flow created within the cell by the influent spray bar.
FIG. 7B is a front elevational view with parts broken away, similar to FIG. 7A, except wherein a biofilm of diatom algae has begun to cover the photocontactor wall.

The filtration system 30 also includes an influent spray bar 60. As best seen in FIG. 2A and FIG. 5B, the spray bar enters the chamber 34 perpendicularly through the intermediate wall 40, extends above and traverses the cells 50, and extends perpendicularly over each of the photocontactor walls 52. As illustrated in FIG. 5B and FIG. 6, the spray bar 60 is substantially cylindrical, and has an upper edge 60U and a lower edge 60L. The spray bar 60 is fed by an influent tube 61. A plurality of spray openings 62 are located in the lower edge 60L. In particular, each of the spray openings 62 is located directly above and centered on one of the cells 50. The spray openings 62 are thereby configured to provide a high velocity stream of water directly into the cells, creating a swirling motion around the diverter 54 therein. In particular, referring to FIG. 7A showing one of the cells 50, the downward stream of water from the spray opening 62 is deflected by the chamber 34 and creates a circuitous water flow 100 within the cell 50 around the diverter 54. To facilitate this, the chamber 34 has an upper bottom 34C that is curved upwardly between the first side 321 and second side 322 to smooth the intersection of the housing bottom 32B and the housing first side 321 as well as the intersection of the housing bottom 32B and the housing second side 322. By avoiding sharp corners that can interfere with the circuitous water flow, the upper bottom 34C creates a smooth "racetrack" of water flow around the diverter 54 that is fed and promoted by the high velocity water exiting the spray opening 62.

The cells 50 provide an ideal environment for cultivating diatom growth. In particular, the filtration system 30 is configured to cultivate the growth of photosynthetic algae, specifically the class called bacillariophyta—commonly called diatoms. The high velocity swirling water in the cells facilitates nutrient absorption by the diatoms. The high intensity light from the light source 44 facilitates accumulation of a biofilm of diatoms on the surfaces within the growth chamber 34, including the photocontactor walls 52. The transparent nature of components of the housing, especially the photocontactor walls 52, and the edgewise illumination of the photocontactor walls 52 facilitate light propagating through the growth chamber 34 and reaching the diatoms—even when surfaces of the photocontactor walls 52 are covered by biofilm. And most importantly, the proliferation of diatoms within the growth chamber 34 prevents undesirable growth of algae elsewhere in the aquarium.

Figure 7C:
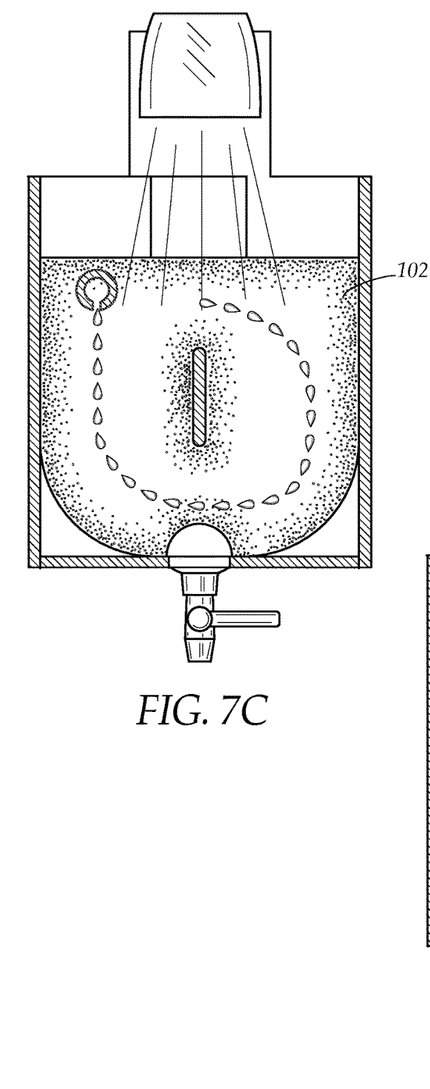
FIG. 7C is a front elevational view with parts broken away, similar to FIG. 7B, except wherein a biofilm of diatom algae has continued to cover the photocontactor wall.
Figure 7D:
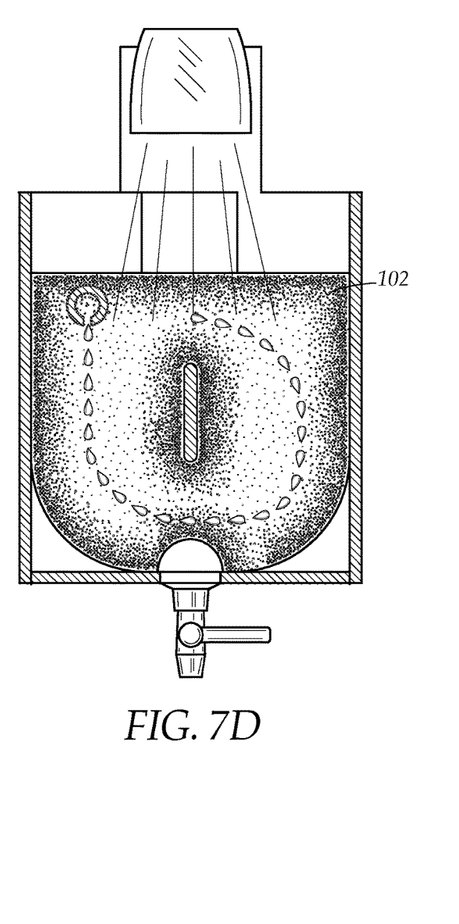
FIG. 7D is a front elevational view with parts broken away, similar to FIG. 7C, except wherein a biofilm of diatom algae has further covered the photocontactor wall.

Referring then to FIG. 7B, with the circuitous water flow 100 continuing within the cell 50 and the high intensity light entering the chamber from the light source 44, diatom proliferation within the chamber 34 begins to create a biofilm 102 on the photocontactor walls 52, as well as other surfaces within the chamber 34, such as the first side 321, second side 322, and the upper bottom 34C. As illustrated in FIGS. 7C and 7D, growth of the biofilm 102 will continue to progress until all surfaces are covered. The transparent nature of the housing—especially the photocontactor walls 52—allows such growth to continue even when it would otherwise have been halted by an insufficient light to the diatoms due to light being blocked by the biofilm itself.

Figure 3:
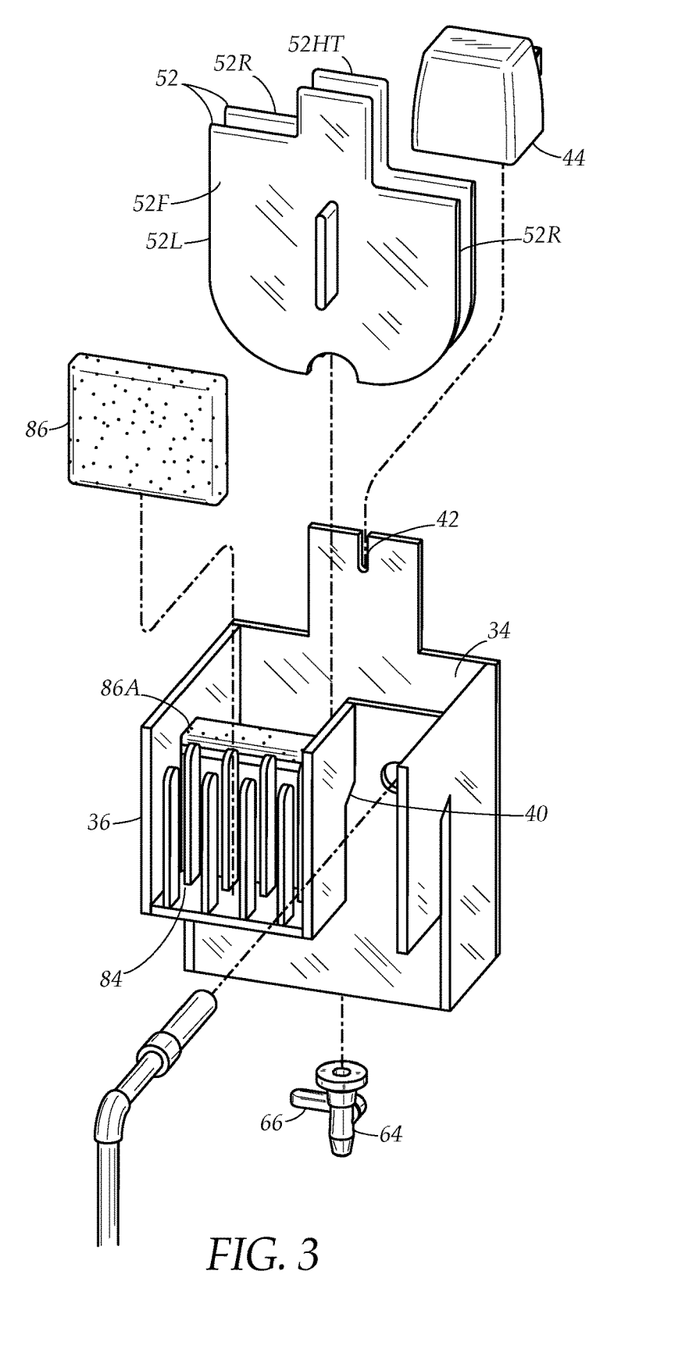
FIG. 3 is an exploded view, illustrating various components of the filtration system in association with the housing.
Figure 4:
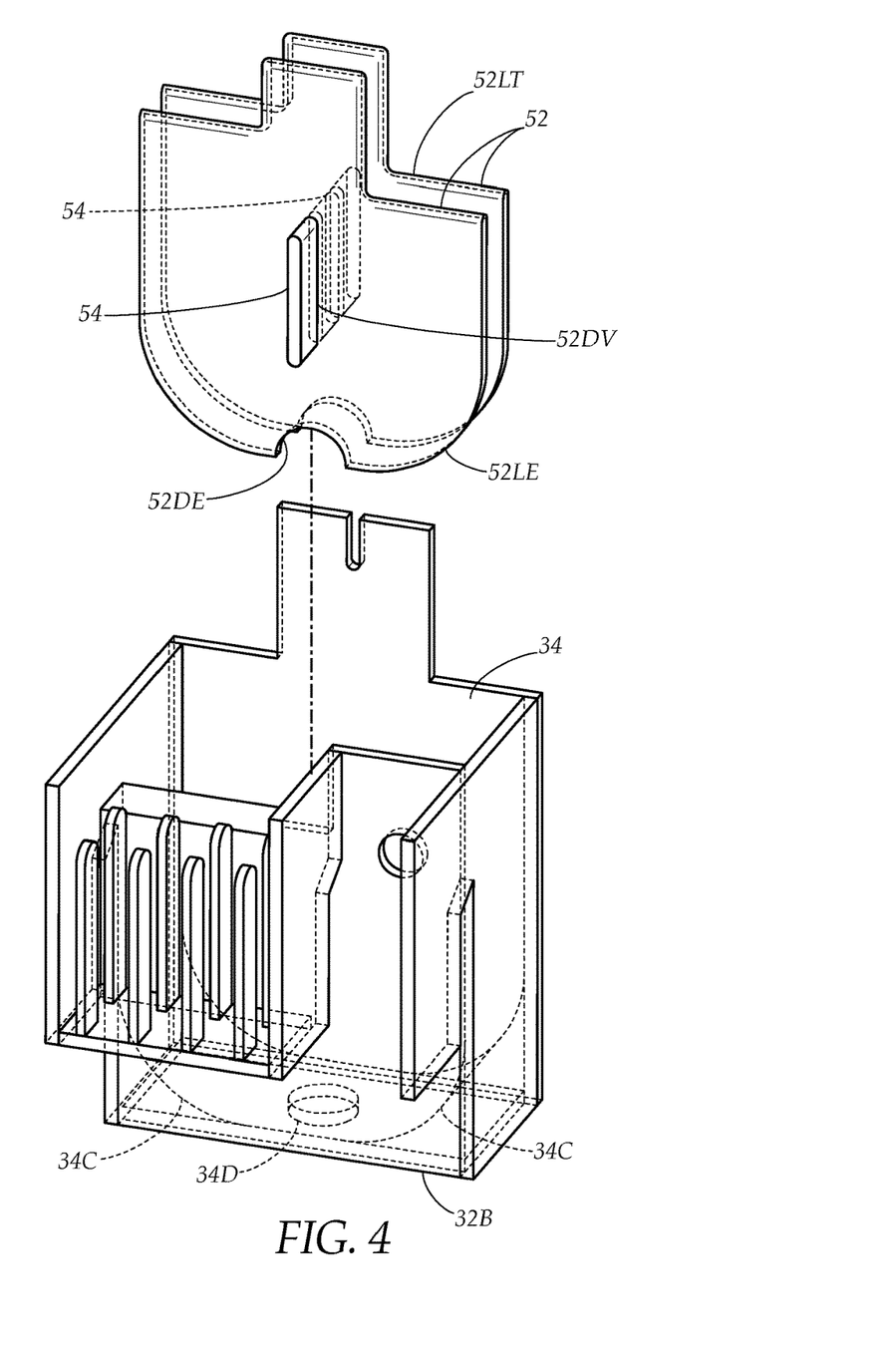
FIG. 4 is an exploded view, illustrating a pair of photocontactor walls/plates, attached together with the diverter, being lowered into the growth chamber of the housing.
Figure 5A:
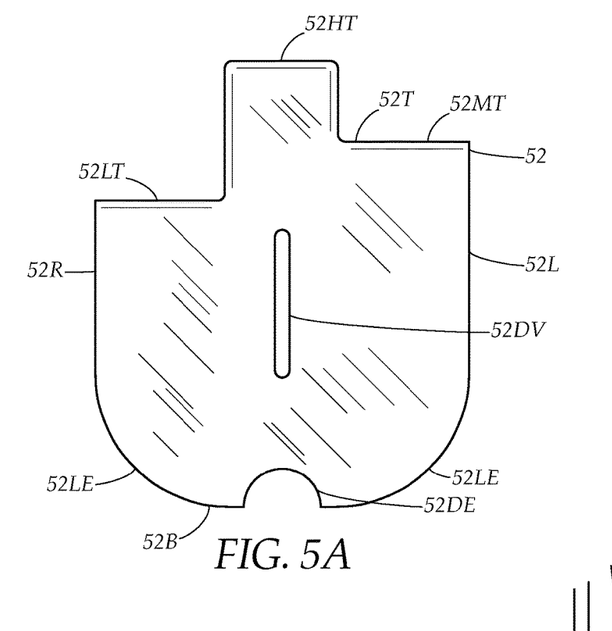
FIG. 5A is a front elevational view, illustrating one of the photocontactors, per se.

Referring to FIGS. 3, 4, and 5A, additional construction and configuration details of the filtration system 30 are illustrated. In particular, each photocontactor wall 52 is a substantially flat and transparent plate having a front 52F, a rear 52R, a substantially uniform thickness between the front 52F and rear 52R; a left side 52L a right side 52R, a bottom 52B, and a multilevel top 52T. The multilevel top includes a mid top 52MT near the left side 52L, a low top 52LT near the right side 52R, and a high top 52HT between the low top 52LT and mid top 52MT. The high top 52HT is configured to extend upwardly near to the output end 44E of the light source 44, well above the water level, providing a light interface that facilitates light entering edgewise into the photocontactor wall 52 and propagate therethrough. Indenting the low top 52LT at a lower height than the mid top 52MT is configured to allow the spray bar 60 to extend over the photocontactor wall 52 at the low top 52LT. The water level within the chamber 34 is generally just above the mid top 52MT. Thus the indenture of the low top 52LT allows the spray bar 60 to be submerged beneath the water level.

Referring to FIGS. 4 and 5A, each photocontactor wall 52 also has a curved lower edge 52LE that is curved between the left side 52L and bottom 52B as well as between the bottom 52B and right side 52R. The curved lower edge 52LE is also configured to match the curvature of the upper bottom 34C of the chamber 34. The photocontactor wall 52 has a drainage cutout 52DE at the bottom 52B that allows flow between the front 52F and rear 52R at the bottom 52B when the chamber 34 is drained as will be described in further detail hereinbelow. The photocontactor wall also has an oval-shaped diverter cutout 52DV that is substantially centered between the left side 52L and right side 52R. As seen in FIG. 4, the diverter 54 has a cross sectional shape that is the same oval shape and size as the diverter cutout 52DV. Thus, the diverter 54 extends through the diverter cutouts 52DV of all of the photocontactor walls 52.

Referring to FIG. 1, during normal operation, a pump 70 intakes water from the tank interior 13 and sends pressurized water through the influent tube 61 to the spray bar 60. From the spray bar 60, pressurized water is released at high velocity into the chamber 34. Preferably, water is introduced at a rate of approximately six hundred times the volume of the growth chamber per hour, or to replace all of the water in the chamber about every six seconds. As additional water is introduced into the chamber 34, water will overflow into the overflow part 36 where it will reenter the tank interior 13. Accordingly, referring to FIG. 2 and FIG. 2A, overflow part 36 has an effluent opening 36A at the housing front 32F. Additional mechanical filtration may be performed within the overflow part 36 prior to reintroducing water to the tank interior 13. In particular, the overflow part may include a pair of finger rows 80 that each include a plurality of fingers 82 that extend upwardly from the overflow bottom 36B and have space therebetween to allow water flow. The finger rows 80 extend parallel to the housing front 32F and intermediate wall 40 as well as parallel to each other. A filter space 84 between the finger rows 80 allows a generally rectangular prism shaped mechanical filter element 86 to fit snugly therebetween, the mechanical filter element 86 being removably contained in said filter space 84. Referring to FIG. 3, the mechanical filter element 86 may be easily removed from between the finger rows 80 for cleaning. An additional mechanical filter element 86A may be provided on top of the intermediate wall 40, such that overflowing water from the chamber 34 into the overflow part 36 will pass through the additional mechanical filter element 86A and be filtered thereby.

Best seen in FIG. 4, the chamber 34 has a drain opening 34D that extends upwardly from the housing bottom 32B and into the chamber 34 to provide fluid communication therewith. Located at a minimal point within the curved upper bottom 34C of the chamber 34, all water within the chamber can drain outwardly therethrough. Accordingly, as seen in FIG. 3 and FIG. 7A, a drain valve 64 is fitted within the drain opening 34D and has a drain control lever 66. The drain valve 64 selectively allows and prevents water from draining from the chamber 34 through the drain opening 34. Accordingly, when the photocontactor walls 52 and other interior surfaces of the chamber 34 become significantly coated with biofilm, a cleaning operation may be performed. During the cleaning operation, the pump 70 (FIG. 1) is turned off, stopping influent water from entering the chamber through the spray bar. The photocontactor walls 52 and other interior surfaces may be mechanically cleaned, scrubbed, or wiped so that the biofilm and other diatom particles are then substantially floating in the water within the chamber. A bucket is positioned under the drain valve 64, and the drain valve 64 is opened by operating the drain control lever 66, allowing water in the chamber 34 to drain into the bucket. Additional cleaning and rinsing may be done prior to closing the drain valve and restarting water flow into the chamber 34 by reactivating the pump.

The apparatus as described hereinabove creates the physical conditions that promote algae growth within the growth chamber, thereby allowing the diatoms to be the dominant algae within the aquarium system, and preventing undesirable algae growth such as on glass panels of the tank. The high intensity light and circuitous high velocity water flow help create the conditions for algae growth. The user may also improve conditions for promoting diatom growth by adding nutrients that make silica the dominant nutrient within the aquarium water, followed by phosphate. It is also important to keep the silica level higher than the level of nitrates in the aquarium water. Accordingly, in a preferred embodiment a silicate added to the water. The silicate is preferably sodium silicate for marine aquariums and potassium silicate for freshwater aquariums. Potassium phosphate as well as chelated iron may be added as consumables to promote growth of the diatoms. The potassium phosphate and chelated iron are added as needed, in conjunction with repeated nitrate testing using a standard hobby grade nitrate testing kit, until nitrates are at an undetectable level. Testing should be repeated regularly to ensure nitrate levels remain undetectable.

It is understood that when an element is referred hereinabove as being "on" another element, it can be directly on the other element or intervening elements may be present therebetween. In contrast, when an element is referred to as being "directly on" another element, there are no intervening elements present.

Moreover, any components or materials can be formed from a same, structurally continuous piece or separately fabricated and connected.

It is further understood that, although ordinal terms, such as, "first," "second," "third," are used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

Spatially relative terms, such as "beneath," "below," "lower," "above," "upper" and the like, are used herein for ease of description to describe one element or feature's relationship to another element(s) or feature(s) as illustrated in the figures. It is understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

Example embodiments are described herein with reference to cross section illustrations that are schematic illustrations of idealized embodiments. As such, variations from the shapes of the illustrations as a result, for example, of manufacturing techniques and/or tolerances, are to be expected. Thus, example embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

In conclusion, herein is presented an aquarium filtration and algae control system. The disclosure is illustrated by example in the drawing figures, and throughout the written description. It should be understood that numerous variations are possible, while adhering to the inventive concept. Such variations are contemplated as being a part of the present disclosure.

What is claimed is:

1. An aquarium filtration and algae control system, for use with an aquarium having a tank having an interior containing a quantity of water and having a frame, the framing having a frame top and having a pump, comprising:
    a housing having an overflow part, a growth chamber and a transition part between the overflow part and growth chamber, the growth chamber has at least two cells that are separated by at least one photocontactor wall that is thereby adjacent to said cells, the at least one photocontactor wall is substantially transparent, the transition part is adapted for supporting the housing upon the frame top of the tank, the overflow part having an effluent opening for reintroducing water from the growth chamber back into the interior of the tank;
    a light source having an output end, the light source attached to the housing and positioned immediately above the cells, the output end directing light toward the cells and the at least one photocontactor wall; and
    a spray bar, adapted to be connected to the pump, the spray bar having a spray opening for each of the at least two cells, said spray opening for each of the at least two cells centered over one of said at least two cells for creating a circuitous water flow within said cells and thereby promoting diatom growth on the at least one photocontactor wall adjacent to said cell.

2. The aquarium filtration and algae control system as recited in claim 1, wherein the housing has a housing front and a housing rear; wherein each photocontactor wall of the at least one photocontactor wall has a front and rear and extends vertically and substantially parallel to the housing front and housing rear, has a left side, a right side, a diverter opening substantially centered between the left side and right side and extending between the front and rear of said photocontactor wall; and further comprising a diverter extending perpendicularly through the diverter opening of each photocontactor wall of the at least one photocontactor wall for directing the circuitous water flow around said diverter.

3. The aquarium filtration and algae control system as recited in claim 2, wherein the housing has a housing first side, a housing second side, a housing bottom, and a drain opening in the housing bottom; and further comprising a drain valve positioned in the drain opening selectively allowing and preventing water from the growth chamber from draining therefrom.

4. The aquarium filtration and algae control system as recited in claim 3, wherein the housing has an upper bottom within the growth chamber, the upper bottom is curved between the housing first side and housing bottom and between the housing second side and housing bottom; wherein each photocontactor wall of the at least one photocontactor wall has a bottom and a curved lower edge that is curved to match and fit snugly within the upper bottom of the growth chamber; and wherein the upper bottom has a minimal point where the drain opening is located.

5. The aquarium filtration and algae control system as recited in claim 4, wherein the growth chamber and overflow part are separated by an intermediate wall that determines a water level within the chamber since water higher than the intermediate wall will enter the overflow part; wherein each of the at least one photocontactor wall has a multi-tiered top surface including a low top adjacent to the spray bar such that the spray bar extends over the low top of each of the at least one photocontactor wall, a mid top located substantially at the water level; and a high top that extends above the water level toward the output end of the light source, the high top providing a light interface that allows edgewise illumination of said photocontactor wall thereat to propagate throughout said photocontactor wall.

6. The aquarium filtration and algae control system as recited in claim 5, wherein the overflow part has an overflow bottom and pair of finger rows that each include a plurality of finger that extend upwardly from the overflow bottom and have a space between the fingers to allow water flow, the finger rows extend parallel to the housing front and intermediate row as well as parallel to each other and define a filter space between the finger rows; and further comprising a rectangular prism shaped mechanical filter element that is removably contained within the finger space.

7. The aquarium filtration and algae control system as recited in claim 6, wherein the at least one photocontactor wall separating at least two cells is at least two photocontactor walls separating at least three cells, wherein the at least two photocontactor walls are spaced apart from each other by the diverter that extends through the diverter openings in said photocontactor walls.

8. An aquarium filtration and algae control system, comprising:
    an aquarium having a tank having an interior containing a quantity of water and having a frame having a frame top and having a pump;
    a housing having an overflow part, a growth chamber and a transition part between the overflow part and growth chamber, the growth chamber has at least two cells that are separated by at least one photocontactor wall that is thereby adjacent to said cells, the at least one photocontactor wall is substantially transparent, the transition part is adapted for supporting the housing upon the frame top of the tank, the overflow part having an effluent opening for reintroducing water from the growth chamber back into the interior of the tank, the housing having an intermediate wall extending between the growth chamber and overflow part, the intermediate wall having a wall height between the growth chamber and overflow part adapted for establishing a water level within the growth chamber;
    a light source having an output end, the light source attached to the housing and positioned immediately above the cells, the output end directing light toward the cells and the at least one photocontactor wall; and
    a spray bar, adapted to be connected to the pump, the spray bar extending into the chamber and over the at least two cells at a level lower than the wall height of the intermediate wall between the overflow part and chamber, the spray bar having a spray opening for each of the at least two cells, said spray opening for each of the at least two cells centered over one of said at least two cells for creating a circuitous water flow within said cells and thereby promoting diatom growth on the at least one photocontactor wall adjacent to said cell.

9. The aquarium filtration and algae control system as recited in claim 8, wherein the housing has a housing front and a housing rear; wherein each photocontactor wall of the at least one photocontactor wall has a front and rear and extends vertically and substantially parallel to the housing front and housing rear, has a left side, a right side, a diverter opening substantially centered between the left side and right side and extending between the front and rear of said photocontactor wall; and further comprising a diverter extending perpendicularly through the diverter opening of each photocontactor wall of the at least one photocontactor wall for directing the circuitous water flow around said diverter.

10. The aquarium filtration and algae control system as recited in claim 9, wherein the housing has a housing first side, a housing second side, a housing bottom, and a drain opening in the housing bottom; and further comprising a drain valve positioned in the drain opening selectively allowing and preventing water from the growth chamber from draining therefrom.

11. The aquarium filtration and algae control system as recited in claim 10, wherein the housing has an upper bottom within the growth chamber, the upper bottom is curved between the housing first side and housing bottom and between the housing second side and housing bottom; and wherein each photocontactor wall of the at least one photocontactor wall has a bottom and a curved lower edge that is curved to match and fit snugly within the upper bottom of the growth chamber.

12. The aquarium filtration and algae control system as recited in claim 11, wherein the growth chamber and overflow part are separated by an intermediate wall that determines a water level within the chamber since water higher than the intermediate wall will enter the overflow part; wherein each of the at least one photocontactor wall has a multi-tiered top surface including a low top adjacent to the spray bar such that the spray bar extends over the low top of each of the at least one photocontactor wall, a mid top located substantially at the water level; and a high top that extends above the water level toward the output end of the light source, the high top providing a light interface that allows edgewise illumination of said photocontactor wall thereat to propagate throughout said photocontactor wall.

13. The aquarium filtration and algae control system as recited in claim 12, wherein the overflow part has an overflow bottom and pair of finger rows that each include a plurality of fingers that extend upwardly from the overflow bottom and have a space between the fingers to allow water flow, the finger rows extend parallel to the housing front and intermediate wall as well as parallel to each other and define a filter space between the finger rows; and further comprising a rectangular prism shaped mechanical filter element that is removably contained within the finger space.

14. The aquarium filtration and algae control system as recited in claim 13, wherein the at least one photocontactor wall separating at least two cells is at least two photocontactor walls separating at least three cells, wherein the at least two photocontactor walls are spaced apart from each other by the diverter that extends through the diverter openings in said photocontactor walls.

15. An aquarium filtration and algae control method, using an aquarium having a tank having an interior containing a quantity of water and having a frame having a frame top and having a pump, comprising the steps of:

providing a filtration system having a housing having a growth chamber and an overflow part, the growth chamber having at least two cells that are separated by at least one photocontactor wall, the overflow part having an effluent opening in proximity with the interior of the tank;

creating circuitous water flow within the at least two cells by spraying water from the tank interior downwardly into each cell;

illuminating the cells with a visible light source; and reintroducing water into the interior of the aquarium through the effluent opening by overflowing water from the growth chamber into the overflow chamber.

16. The aquarium filtration and algae control method as recited in claim 15, wherein the filtration system has a spray bar that extends into the chamber across the at least two cells, the spray bar has an opening centered over each of the at least two cells, and wherein the step of spraying water downwardly into the cell further comprises spraying water from the opening centered over each cell into said cell.

17. The aquarium filtration and algae control method as recited in claim 16, further comprising the step of adding a silicate selected from the group consisting of potassium silicate and sodium silicate to the aquarium water.

18. The aquarium filtration and algae control method as recited in claim 17, further comprising the step of adding potassium phosphate and chelated iron to the aquarium water.

19. The aquarium filtration and algae control method as recite in claim 16, wherein the chamber has a curved upper bottom surface having a minimal point and having a drain valve located at the minimal point, and wherein the steps as recited further comprise the steps of:

discontinuing spraying water into the cells;

cleaning biofilm from the photocontactor walls by wiping the photocontactor walls;

draining the chamber by opening the drain valve; and reinitiating spraying water into the cells after closing the drain valve.

20. The aquarium filtration and algae control method as recited in claim 19, wherein the at least two cells is three cells and the at least one photocontactor wall is two photocontactor walls that separate the three cells; wherein each photocontactor wall has a high top that extends above the water line near the light source; and wherein the step of illuminating the cells further comprises propagating light through the photocontactor walls by illuminating edgewise each photocontactor wall at the high top of said photocontactor wall.

* * * * *